United States Patent [19]

Watanabe et al.

[11] Patent Number: 5,091,417

[45] Date of Patent: Feb. 25, 1992

[54] PREVENTIVE AND THERAPEUTIC AGENT FOR HEPATITIS

[75] Inventors: Masahiro Watanabe; Kazumasa Yokoyama, both of Hirakata, Japan

[73] Assignees: The Green Cross Corporation, Osaka; Taisho Pharmaceutical Co., Ltd., Tokyo, both of Japan

[21] Appl. No.: 579,956

[22] Filed: Sep. 10, 1990

[30] Foreign Application Priority Data

Sep. 11, 1989 [JP] Japan .................. 1-235386

[51] Int. Cl.$^5$ .................. A61K 31/19; A61K 31/215
[52] U.S. Cl. .................. 514/530; 514/573
[58] Field of Search .................. 514/573, 530

[56] References Cited

U.S. PATENT DOCUMENTS 4,849,451  7/1989  Mizushima et al. .................. 514/530

OTHER PUBLICATIONS

Abecassis et al., Treatment of Fulminant Hepatic Failure with a Continuous Infusion of Prostin VR (PGE 1) (Abstract), Hepatology, vol. 7, No. 5, 1987, p. 1104.

Mizoguchi et al., The Protective Effects of Prostaglandin E1, in an Experimental Massive Hepatic Cell Necrosis Model, Hepatology, No. 7, No. 6, 1987, pp. 1184–1188.

Primary Examiner—Stanley J. Friedman
Attorney, Agent, or Firm—Cushman, Darby & Cushman

[57] ABSTRACT

A preventive and therapeutic agent for hepatitis, comprising a fat emulsion containing a compound having prostaglandin $E_1$ activities.

9 Claims, No Drawings

PREVENTIVE AND THERAPEUTIC AGENT FOR HEPATITIS

BACKGROUND OF THE INVENTION

1. Field of the Invention

This invention relates to a novel use of a fat emulsion containing a compound having prostaglandin $E_1$ activities, more particularly to a preventive and therapeutic agent for hepatitis using such a fat emulsion.

2. Description of the Prior Art

Fluminant hepatitis is developed at the time when acute hepatitis has been proceeded (rate of development being about 2%). Fluminant hepatitis is caused by hepatic virus etc. and is typified by rapid development of symptoms of hepatic insufficiency. A high percentage of the patients suffering from this disease die from hepatic coma in some to 10 days after development of the symptoms.

Since its mechanism of genesis is still unknown, no effective method of treatment for this disease has yet been found. Accordingly, no causal therapy for this disease has been established, and the only clinical treatments which are actually practiced are exchange of blood plasma or replacement transfusion for hepatic encephalopathy (coma), glucagon-insulin therapeutics for hepatic regeneration, and other certain symptomatic therapies such as steroid therapy.

As a result of many studies on the problems mentioned above, the present inventors found that a fat emulsion containing a compound having prostaglandin $E_1$ (hereinafter referred to as $PGE_1$) activities is not only potent against fulminant hepatitis but also more widely useful for the treatment of many types of hepatitis. The present invention has been attained on the basis of this finding.

SUMMARY OF THE INVENTION

The preventive and therameputic agent for hepatitis according to the present invention comprises a fat emulsion containing a compound having $PGE_1$ activities.

DETAILED DESCRIPTION OF THE INVENTION

The compounds having $PGE_1$ activities usable in the present invention include all the compounds which have $PGE_1$ activities and are pharmaceutically acceptable ones. $PGE_1$ and its derivatives are typical examples.

The $PGE_1$ derivatives usable in this invention are the ones which have $PGE_1$ activities and are suited for use as a pharmaceutical component. For examples, the $PGE_1$ derivatives disclosed in U.S. Pat. No. 4,849,451 and Japanese Patent Application (Laid-open) No. 59-216820 are preferred.

The above-mentioned $PGE_1$ and its derivatives are those represented by the general formula

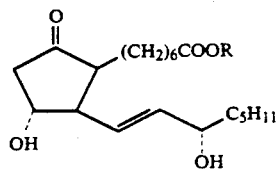

wherein R denotes hydrogen and an alkyl group having 1 to 30 carbon atoms respectively.

The alkyl group in the above general formula may be of either straight chain or branched chain. The number of its carbon atoms is 1 to 30, preferably 1 to 15 and more preferably 3 to 10. Examples of such alkyl groups include methyl, ethyl n-propyl, isopropyl, n-butyl, isobutyl, tert-butyl, n-pentyl, n-hexyl, n-heptyl, n-octyl, n-nonyl and n-decyl.

A fat emulsion containing a compound having $PGE_1$ activities, which constitutes active ingredient of the preventive and therameputic agent for hepatitis according to the present invention, may comprise, for instance, 5 to 50, preferably 10 to 20% (W/V) of a vegetable oil, 1 to 50, preferably 5 to 30 parts by weight of phospholipid for 100 parts by weight of the vegetable oil, a proper quantity of water, and an effective quantity of a compound having $PGE_1$ activities. The fat emulsion may be added, if necessary, with 0.3% (W/V) or less of an emulsifier adjuvant, 5% (W/V) or less of a stabilizer, a polymeric substance as stabilizing adjuvant in an amount of 0.1 to 5, preferably 0.5 to 1 parts by weight to 1 part of the compound having $PGE_1$ activities (i.e. $PGE_1$ or $PGE_1$ derivative), and 0.1-10% (W/V) of an isotonizing agent (for example, glycerin and glucose). The content of the compound having $PGE_1$ activities in the fat emulsion can be properly varied depending on the form of emulsion, the way of administration, etc., but usually said compound is contained in an amount of 0.2 to 100 μg/ml in the emulsion.

The vegetable oil to be added to said fat emulsion include soybean oil, sesame oil, castor oil, cottonseed oil and olive oil, and soybean oil is preferred. It is more preferred to use a highly purified soybean oil, particularly preferably a high-purity soybean oil (purity: 99.9% or above as tri-, di- and mono-glyceride) obtained by further purifying the commonly purified soybean oil by steam distillation or other like means.

As phospholipid, there can be used purified phospholipid such as egg yolk phospholipid and soybean phospholipid, and it can be prepared by ordinary fractionation method using an organic solvent. For instance, crude egg yolk phospholipid is dissolved in a cold n-hexane-acetone mixed solvent, slowly adding acetone thereto with stirring, followed by filtering-out of insolubles, and after repeating this operation once more, the solvent is distilled off to obtain the desired purified phospholipid. The thus obtained phospholipid mainly consists of phosphatidyl choline and phosphatidyl ethanolamine. It also contains other phospholipids such as phosphatidyl inositol, phosphatidyl serine, sphingomyelin and the like in smaller quantities.

Further, there can be also used egg yolk phospholipid from which phosphatidyl ethanol amine has been eliminated. A method for its production has been disclosed in U.S. Pat. No. 4,684,633.

The emulsifying adjuvant includes fatty acids of 6 to 22, preferably 12 to 20 carbon atoms which are pharmaceutically acceptable. These fatty acids may be of either straight chain or branched chain, but straight-chain stearic acid, oleic acid, linolic acid, palmitic acid, linolenic acid, myristic acid and the like are preferred. It is also possible to use their pharmaceutically acceptable salts such as alkali metal salts (sodium salt, potassium salt, etc.) and alkaline earth metal salts (calcium salt, etc.).

The stabilizer includes cholesterols and phosphatidic acid which are pharmaceutically usable, and are used in an amount of 0.5, preferably 0.1% (W/V) and in an amount of 5, preferably 1% (W/V), respectively.

The polymeric substance includes albumin, dextran, vinyl polymer, nonionic surfactant, gelatin and hydroxyethyl starch, and preferred types of albumin, vinyl polymers and nonionic surfactants usable as polymeric substance are as follows. Albumin should be of the human origin in consideration of antigenicity.

A typical example of vinyl polymers is polyvinylpyrrolidone.

As nonionic surfactant, there can be used polyalkylene glycol (for example, polyethylene glycol having an average molecular weight of 1,000 to 10,000, preferably 4,000 to 6,000), polyoxalkylene copolymers (for example, polyoxyethylene-polyoxypropylene copolymer having an average molecular weight of 1,000 to 20,000, preferably 6,000 to 10,000), hardened castor oil polyoxyalkylene derivatives [for example, hardened castor oil polyoxyethylene-(40), -(20) and -(100) ether], and castor oil polyoxyalkylene derivatives [for example, castor oil polyoxyethylene-(20), -(40) and -(100) ether].

Glycerin or glucose used as isotonizing agent in this invention is a pharmaceutically acceptable one.

The fat emulsion used in the present invention can be prepared by the various methods. For example, it can be produced in the following way.

Predetermined amounts of a vegetable oil (preferably soybean oil), phospholipid, a compound having $PGE_1$ activities, and other additives such as mentioned above are mixed and added with a necessary amount of water. This solution is homogenized by a commonly used homogenizer (such as a pressure-jet type homogenizer or an ultrasonic homogenizer) to prepare an oil-in-water type emulsion, whereby a desired fat emulsion is produced. The thus produced fat emulsion may be further added with a stabilizer, isotonizing agent and other additive(s) if necessary for the reasons relating to formulation. The preventive and therapeutic agent for hepatitis of this invention comprising said fat emulsion is usually administered by intravenous injection, continuous drip infusion, or in other appropriate ways. The agent is generally given at a dose of about 0.1 to 20 μg/kg body weight, preferably 1 to 10 μg/kg body weight, in terms of quantity of active ingredient, in one administration for adults, but the dose may be properly adjusted according to the condition of the patient, the region of application, etc.

The preventive and therapeutic agent for hepatitis according to the present invention is considered to be particularly effective for the treatment of fulminant hepatitis. The present agent, however, has potenties for various types of hepatitis; it is not only efficaceous against fulminant hepatitis but also effective for the treatment of viral hepatitis, alcoholic hepatitis, drug-induced hepatitis, acute and chronic hepatitis, and useful for the prevention of hepatic insufficiency, hepatocirrhosis and other hepatic troubles.

The preventive and therapeutic agent for hepatitis of this invention is capable of retaining its efficacy for a long time in the living body and can produce a sufficient action with a small dose. This effect is more remarkable than the $PGE_1$ cyclodextrin clathrate. Thus, by use of the agent of the present invention, it is possible to decrease the effective dose and to realize reduction of side effects. The present agent therefore is of extremely high clinical utility for the prevention and therapeutics of heptatitis.

The prevent invention will be described more particularly by showing the examples and test examples However, these examples are merely illustrative and do not limit the scope of the invention.

EXAMPLE 1

3.6 g of purified egg yolk phospholipid, 900 μg of $PGE_1$, 0.15 g of sodium palmitate and 0.15 g of phosphatidic acid were added to 30 g of purified soybean oil and they were dissolved by heating. To this solution was added 200 ml of distilled water for injection and then 7.5 g of glycerin of official grade (Pharmacopoeia of Japan). The resultant solution was further added with distilled water for injection to make the total amount of the solution 300 ml and emulsified by a homomixer to prepare a crude emulsion.

This crude emulsion was passed through Manton-Gaulin homogenizer under high pressure, whereby a fat emulsion containing homogenized, extremely fine $PGE_1$ particles could be obtained (this fat emulsion is hereinafter referred to as $PGE_1$-lipo). This emulsion had an average particle diameter of 0.2 to 0.4 μ.

EXAMPLE 2

A fat emulsion was prepared in the same way as in Example 1 except that 0.15 g of sodium oleate was used in place of 0.15 of sodium palmitate and 0.15 g of phosphatidic acid.

TEST EXAMPLE 1

Life-saving effect on laboratory acute hepatic insufficiency-affected mice

The heat-killed cells of Propionibacterium acnes (P. acnes), which is a Gram-positive anaerobe, were intravenously injected (tail vein), at a rate of 1 mg/mouse, to the Balb/c strain male mice (6 to 8 weeks old, divided into groups of 10). 7 days thereafter, lipopolysaccharide (LPS) derived from a Gram-negative bacterium was intravenously injected (tail vein) at a rate of 1 μg/mouse to induce acute hepatic insufficiency. Then $PGE_1$-lipo prepared in Example 1 was intravenously injected (tail vein) (at a dose of 0.25 μg/mouse and 0.5 μg/mouse in terms of the quantity of $PGE_1$) to the test mice just before giving LPS, and the rate of survival of the mice after the lapse of 24 hours was examined. To the mice in the comparative control group, cyclodextrin clathrate of $PGE_1$ ($PGE_1$-CD) was intravenously injected (at a dose of 0.5 μg/mouse in terms of quantity of $PGE_1$) in the same way as described above, and the survival rate was compared with another control group to which a physiological saline solution was given. The results are shown in Table 1.

The results of Table 1 evidently attest to the remarkable life-saving effect of $PGE_1$-lipo for the mice suffering from acute hepatic insufficiency.

TABLE 1

| Specimen | Rate of survival (%) | |
|---|---|---|
| | 10 hrs. after giving LPS | 24 hrs. after giving LPS |
| Physiological saline solution (control) | 20 | 10 |
| $PGE_1$-lipo (0.25 μg/animal) | 50 | 30 |
| $PGE_1$-lipo (0.5 μg/animal) | 80 | 60 |
| $PGE_1$-CD (0.5 μg/animal) | 40 | 10 |

LPS administered 7 days after giving *P. acnes,* and each specimen was administered just before giving LPS.

Endotoxin is considered to play an important role against a rapid development of symptoms of hepatic insufficiency. As Test Example 1 shows, by administering heated-killed *P. acnes,* monocitosis is induced in the liver. A further administration of endotoxin causes apparent necrosis of the liver, which proceeds to death. The present drug showed very strong life-saving effects against such hepatic insufficiency.

TEST EXAMPLE 2

Effect on guinea pigs affected by immunological hepatic insufficiency cytotoxic trouble 2.25 ml of a hepatic homogenate supernatant fraction (4 mg/ml) treated with sodium 2,4,6-trinitrobenzenesulfonate (TNP) was administered along with an equal amount of Freund complete adjuvant (FCA) subcutaneously to the heels of guinea pigs (body weight: 400–500 g; divided into groups of 10). 2 weeks thereafter, $5 \times 10^6$ TNP-treated liver cells were given into the mesentric vein to induce immunological hepatic insufficiency cytotoxic trouble. Then $PGE_1$-lipo prepared in Example 1 was administered intravenously (0.05 μg/animal, 0.1 μg/animal and 0.2 μg/animal in terms of quantity of $PGE_1$) just before giving the TNP-treated liver cells, and 24 hours thereafter, the effect on rise of serum GOT and GPT was investigated. A physiological saline solution was given to the comparative control group in the similar way. The results are shown in Table 2. GOT of the normal (nontreated) guina pigs was $48 \pm 10$ (IU/l) and GPT thereof was $45 \pm 7$ (IU/l).

As seen from Table 2, $PGE_1$-lipo could strikingly arrest the rise of serum GOT and GPT.

TABLE 2

| Specimen | GOT (IU/l) | GPT (IU/l) |
| --- | --- | --- |
| Physiological saline solution (control) | 344 ± 84 | 56 ± 16 |
| $PGE_1$-lipo (0.05 μg/animal) | 164 ± 28 | 31 ± 14 |
| $PGE_1$-lipo (0.1 μg/animal) | 122 ± 18* | 33 ± 6 |
| $PGE_1$-lipo (0.2 μg/animal) | 72 ± 2** | <5 |

(Notes)
n = 10, average ± S.E.
*P < 0.01 (as against control group)
**P < 0.05 (as against control group)

That immunological action is involved with viral or drug induced hepatic insufficiency is well known. As Test Example 2 shows, strongly immunogenic TNP was sensitized with specific hepatic immunogen, and the TNP-treated liver cells were applied to laboratory animals. The present drug has been found to show strong restraint against the immunological hepatic insufficiency in the animals.

What is claimed is:

1. A method for treating a hepatitis which comprises administering by intravenous injection and continuous drip infusion to a hepatitis patient a fat emulsion containing a compound having prostaglandin $E_1$ activities represented by the general formula

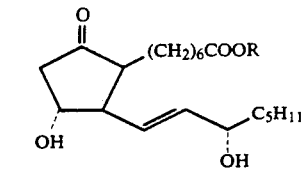

wherein R denotes hydrogen or an alkyl group having 1 to 30 carbon atoms in an amount of 0.2 to 100 μg per ml of the emulsion, 5 to 50% (W/V) of a vegetable oil, 1 to 50 parts by weight of phospholipid for 100 parts by weight of the vegetable oil, and a sufficient amount of water to make said emulsion.

2. A method according to claim 1, wherein the vegetable oil is soybean oil, sesame oil, caster oil, cotton seed oil or olive oil.

3. A method according to claim 2, wherein the vegetable oil is soybean oil.

4. A method according to claim 1, wherein the phospholipid is egg yolk phospholipid or soybean phospholipid.

5. A method according to claim 1, wherein the fat emulsion contains as an emulsifying adjuvant 0.01 to 0.3% (W/V) of fatty acid having 6 to 22 carbon atoms or pharmaceutically acceptable salt thereof.

6. A method according to claim 1, wherein the fat emulsion contains as stabilizer 0.001 to 0.5% (W/V) of a cholesterol or 0.01 to 5% (W/V) of a phosphatidic acid.

7. A method according to claim 1, wherein the fat emulsion contains as stabilizing adjuvant 0.1 to 0.5 parts by weight of at least one polymeric substance selected from the group consisting of albumin, dextran, vinyl polymer, nonionic surfactant, gelatine and hydroxyethyl starch to 1 part by weight of the compound having $PGE_1$ activities.

8. A method according to claim 1, wherein the fat emulsion contains as an isotonizing agent 0.1 to 10% (W/V) of glycerine or glucose.

9. A method according to claim 1, wherein the fat emulsion is given at a dose of 0.1 to 20 μg/kg body weight, in terms of quantity of active ingredient in one administration for adults.

* * * * *